United States Patent
Park et al.

(10) Patent No.: US 10,589,256 B2
(45) Date of Patent: Mar. 17, 2020

(54) SELECTIVE HYDROGENATION CATALYST AND SELECTIVE HYDROGENATION METHOD USING THE SAME

(71) Applicant: Korea Research Institute of Chemical Technology, Daejeon (KR)

(72) Inventors: Ji Hoon Park, Pyeongtaek-si (KR); Kwan Yong Jeong, Daejeon (KR); Soo Min Kim, Daejeon (KR); Tae Sun Chang, Daejeon (KR); Iljeong Heo, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 16/109,664

(22) Filed: Aug. 22, 2018

(65) Prior Publication Data
US 2019/0076826 A1 Mar. 14, 2019

(30) Foreign Application Priority Data
Sep. 12, 2017 (KR) .................. 10-2017-0116248

(51) Int. Cl.
| | | |
|---|---|---|
| *B01J 27/00* | (2006.01) | |
| *B01J 23/46* | (2006.01) | |
| *B01J 37/08* | (2006.01) | |
| *B01J 27/24* | (2006.01) | |
| *C07D 295/027* | (2006.01) | |
| *B01J 37/18* | (2006.01) | |

(52) U.S. Cl.
CPC ............. *B01J 23/462* (2013.01); *B01J 27/24* (2013.01); *B01J 37/08* (2013.01); *B01J 37/18* (2013.01); *C07D 295/027* (2013.01)

(58) Field of Classification Search
CPC ....................................................... B01J 27/00
See application file for complete search history.

(56) References Cited

U.S. PATENT DOCUMENTS
| | | | |
|---|---|---|---|
| 5,648,576 A | 7/1997 | Nguyen Than et al. | |
| 7,459,467 B2 | 12/2008 | Kumar et al. | |

FOREIGN PATENT DOCUMENTS
| | | | | |
|---|---|---|---|---|
| JP | 2004067592 A | 3/2004 | | |
| KR | 1020010102934 A | 11/2001 | | |
| WO | WO-2018048058 A1 * | 3/2018 | ........... | C07D 401/06 |

OTHER PUBLICATIONS

Zhu, J., et al. "Graphitic Carbon Nitride: Synthesis, Properties, and Applications in Catalysis." ACS Appl. Mater. Interfaces. (2014), vol. 6, pp. 16449-16465. (Year: 2014).*

Pierre Fouilloux; The Nature of Raney Nickel, Its Adsorbed Hydrogen and Its Catalytic Activity for Hydrogenation Reactions; Applied Catalysis; vol. 8 (1983) pp. 1-42; Elsevier Science Publishers B.V., Amsterdam, Netherland.

A. V. Sapre et. al; Hydrogenation of Aromatic Hydrocarbons Catalyzed by Sulfided Co0-MoO3/-Al2O3 Reactivities and Reaction Networks; Ind. Eng. Chem. Process Des. Dev. 1981, Vo. 20, pp. 68-73.

* cited by examiner

*Primary Examiner* — Andrew D Kosar
*Assistant Examiner* — John S Kenyon
(74) *Attorney, Agent, or Firm* — STIP Law Group, LLC

(57) ABSTRACT

The present invention relates to a Ru—Pd bimetallic catalyst for use in hydrogenation of a compound, and more particularly to a catalyst prepared by loading both ruthenium and palladium on a g-$C_3N_4$ support and to a selective hydrogenation process of a pyridine group in a reaction system containing both a pyridine group and a benzene group using the catalyst.

6 Claims, 1 Drawing Sheet

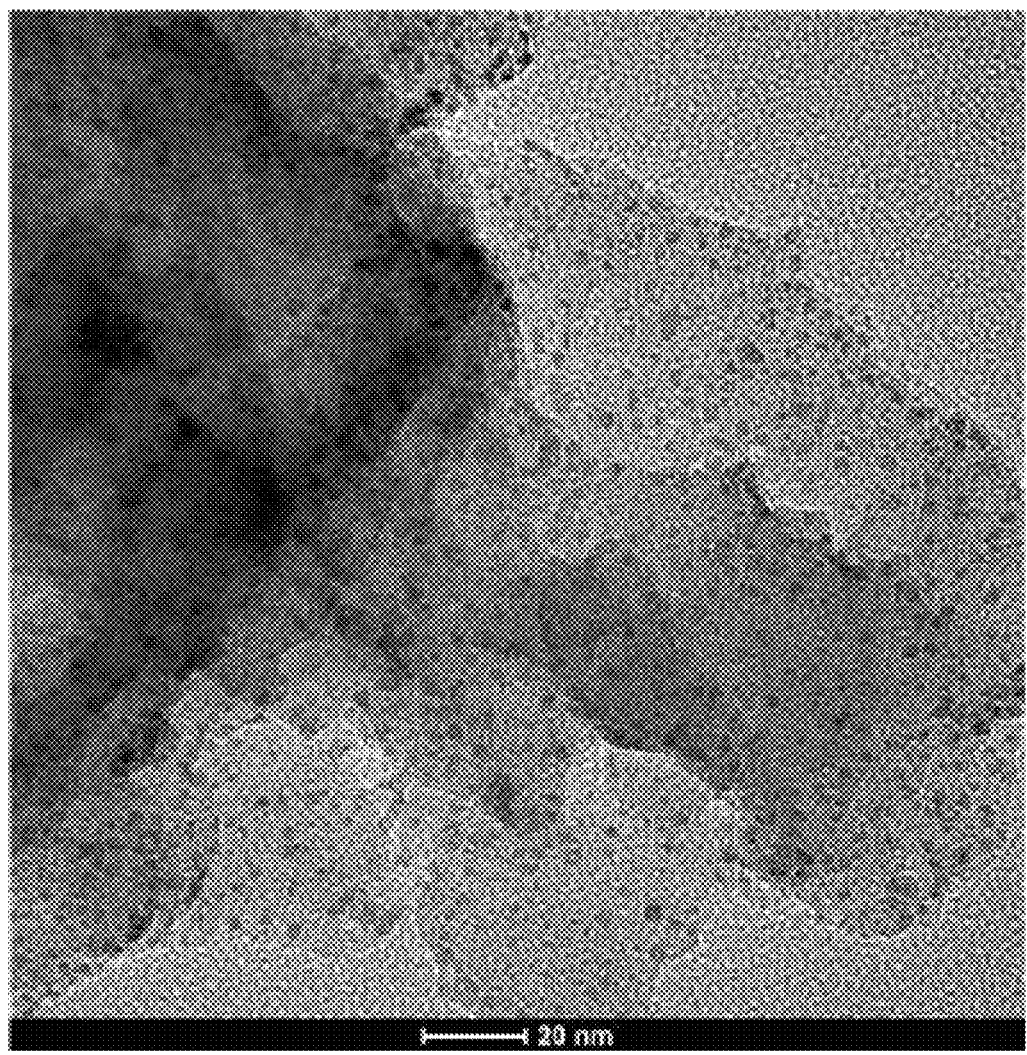

SELECTIVE HYDROGENATION CATALYST AND SELECTIVE HYDROGENATION METHOD USING THE SAME

CROSS-REFERENCE TO RELATED APPLICATION

This application claims the priority the Korean Patent Applications NO 10-2017-0116248 filed on Sep. 12, 2017 in the Korean Intellectual Property Office, the disclosure of which is incorporated herein reference.

BACKGROUND OF THE INVENTION

1. Technical Field

The present invention relates to a ruthenium (Ru)-palladium (Pd) catalyst, which is used to hydrogenate an organic compound having a pyridine group as a functional group, thereby enabling selective hydrogenation of the functional group, and to a selective hydrogenation process using the same.

2. Description of the Related Art

The hydrogenation reaction of an organic compound is a reaction in which hydrogen is added to an unsaturated bond of the organic compound, such as a carbon-carbon double or triple bond, or multiple bonds such as a carbonyl group, and is called a hydro-addition reaction or a hydrogen addition reaction. The hydrogenation reaction is a kind of reduction reaction. This reaction makes it possible to convert unsaturated hydrocarbon into saturated hydrocarbon.

Hydrogenation includes a catalytic hydrogenation process using hydrogen and a catalyst and a chemical reduction process using a hydride reducing agent or the like. Of these, the catalyst for use in the catalytic hydrogenation process mainly contains a metal such as nickel (Ni), cobalt (Co), platinum (Pt), palladium (Pd), rhodium (Rh), etc.

In general, benzene ring hydrogenation of aromatics, which is the most difficult reaction among various hydrogenation reactions, is carried out using a noble-metal-based catalyst such as platinum (Pt), rhodium (Rh), ruthenium (Ru) or palladium (Pd). However, this type of catalyst is not economical due to its high price, and thus many attempts have been made to replace it. In particular, Raney Nickel (Applied Catalysis Vol. 8 (1983) pp. 1-42) or a catalyst such as cobalt (Co), molybdenum (Mo) or aluminum (Al) oxide (Ind. Eng. Chem. Process Des. Dev. Vol. 20, No. 1 (1981), pp. 68-73) has have been utilized for hydrogenation, but are problematic because they can have low conversion and selectivity, and many byproducts are produced by decomposition.

Furthermore, in hydrogenation reaction, selective hydrogenation reactions in which the only one of the two types of functional groups that enable hydrogenation are selectively hydrogenated are regarded as very important in synthetic chemistry.

For example, a palladium/carbon (Pd/C) catalyst is widely used for selective hydrogenation of an unsaturated organic compound. The palladium/carbon (Pd/C) catalyst is advantageous because the production process is simple, the conversion rate, yield, and selectivity are high, and selective removal of the catalyst becomes possible after termination of the reaction. Accordingly, this catalyst is favored by many companies, and is utilized in a variety of fields of petrochemicals, fine chemicals, and pharmaceutical production processes.

Several other documents address the performance enhancement of palladium-based supported catalysts, particularly in the hydrogenation of alkyne such as acetylene. For example, U.S. Pat. No. 5,648,576 discloses a gas-phase selective hydrogenation process of an acetylene compound containing 2 or 3 carbon atoms into an ethylene compound using a supported catalyst surface-modified with Pd and a metal of Group 1B, for example, Ag, and optionally, an alkali metal or an alkaline earth metal, in the presence of hydrogen. The selective hydrogenation of acetylene is typically carried out using a feed containing 98% ethylene and 2% acetylene at a space velocity of 3300 $h^{-1}$ (Patent Document 1).

As for the intramolecular selective hydrogenation of an aromatic compound, U.S. Pat. No. 7,459,467 discloses an intramolecular selective hydrogenation method of synthesizing a methylphenidate derivative by selectively hydrogenating a pyridine group using a palladium/carbon (Pd/C) catalyst. The intramolecular selective hydrogenation reaction is carried out using a compound containing both a pyridine group and a benzene group in a solvent comprising organic acid or inorganic acid and alcohol (Patent Document 2).

Also, Japanese Patent Application Publication No. 2004-067592 discloses the selective hydrogenation of a pyridine group in a molecule by inducing a hydrogenation reaction of amino-phenylpyridine using a catalyst containing palladium (Pd) and platinum (Pt) and an organic carboxylic acid solvent, consequently yielding amino-phenylpiperidine (Patent Document 3).

Korean Patent Application Publication No. 10-2001-0102934 discloses a method of preparing piperidine through catalytic hydrogenation of pyridine using a palladium-on-carbon catalyst and an aromatic hydrocarbon solvent. Aromatic hydrocarbons, such as benzene, toluene, xylene and other alkyl aromatic compounds, may be added as the solvent for catalytic hydrogenation of pyridine, thereby obtaining piperidine having high purity through the catalytic hydrogenation of pyridine (Patent Document 4).

As confirmed in Patent Documents 2 to 4, the selective hydrogenation of the pyridine group in the hydrogenation reaction of the benzene group and the pyridine group using the palladium catalyst has been known, but in order to obtain high-purity compounds at high yield, the development of a catalyst having high hydrogenation selectivity is required.

Furthermore, examples of the support for loading an active metal are known to be activated carbon, silica gel, aluminum oxide and calcium carbonate, but research into the effect of the support composition on the reaction depending on the type of active metal under the specific reaction conditions is insufficient.

Moreover, the present invention may be applied to a reversible hydrogenation method performed on a substrate having a functional group capable of storing and releasing hydrogen at an actual operating temperature and pressure, particularly storing hydrogen. Hydrogen is a chemical material widely used in the chemical and petroleum processing industries, and is recently receiving attention as a green energy source due to the development of fuel cells using hydrogen as a feed.

Fixed fuel cells may be directly supplied with hydrogen through a local natural gas reformer or a hydrogen pipeline. However, the internal fuel cell or hydrogen fuel internal combustion engine of a mobile transport system requires a practical and effective method of storing hydrogen.

Hydrogen may be stored in a compressed form in a high-pressure tank suitable for storage at a maximum pressure of 875 bar. Also, hydrogen may be stored in the form of low-temperature liquefied hydrogen in a suitable cryogenic vessel, preferably a super-insulated cryogenic vessel.

Meanwhile, as a way to store hydrogen, the chemical reaction system is in the experimental stages, and hydrogen is stored in an organic compound that is capable of being hydrogenated and may chemically bond with hydrogen.

The present inventors have ascertained that selective hydrogenation is performed at high efficiency when a catalyst comprising a combination of specific metals and a combination of specific supports is used among catalysts responsible for selective hydrogenation at a high yield compared to currently useful catalysts in the selective hydrogenation reaction, thus culminating in the present invention.

CITATION LIST

Patent Literature (Patent Document 1) U.S. Pat. No. 5,648,576 (Institut Francais du Pétrole) Jul. 15, 1997

(Patent Document 2) U.S. Pat. No. 7,459,467 (IPCA Laboratories, Ltd.) Dec. 2, 2008

(Patent Document 3) Japanese Patent Application Publication No. 2004-067592 (KOEI CHEM Co. Ltd.) Mar. 4, 2004

(Patent Document 4) Korean Patent Application Publication No. 10-2001-0102934 (Bayer Aktiengesellschaft) Nov. 17, 2001

SUMMARY OF THE INVENTION

Accordingly, an aspect of the present invention is to provide a Ru—Pd/g-$C_3N_4$ hydrogenation catalyst having high reaction selectivity and a selective hydrogenation process using the same.

The other aspects of the present invention will be able to be clearly understood through the following description and to be realized by experts and researchers in the art.

Therefore, the present invention provides a selective hydrogenation catalyst, in which ruthenium and palladium as active components are loaded on a g-$C_3N_4$ support so that the sum of weights of the active components is 0.1 to 15 wt % based on the total weight of the catalyst including the support and which is used to selectively hydrogenate a pyridine compound represented by Chemical Formula 2 below in a mixture comprising a benzene compound represented by Chemical Formula 1 below and the pyridine compound represented by Chemical Formula 2.

[Chemical Formula 1]

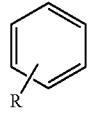

[Chemical Formula 2]

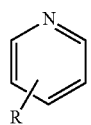

In Chemical Formulas 1 and 2, R is hydrogen, a $C_1$-$C_{13}$ alkyl or cycloalkyl group, a $C_7$-$C_{13}$ arylalkyl group, $C_1$-$C_{13}$ alkyl alcohol or $C_1$-$C_{13}$ alkylether.

In addition, the present invention provides a selective hydrogenation catalyst, in which ruthenium and palladium as active components are loaded on a g-$C_3N_4$ support so that the sum of weights of the active components is 0.1 to 15 wt % based on the total weight of the catalyst including the support and the weight ratio b/a of ruthenium b relative to palladium a ranges from 0.25 to 10, and which is used to selectively hydrogenate the pyridine compound represented by Chemical Formula 2 in a mixture comprising the benzene compound represented by Chemical Formula 1 and the pyridine compound represented by Chemical Formula 2.

In addition, the present invention provides a method of preparing a selective hydrogenation catalyst, comprising: a) preparing a support solution by dispersing a g-$C_3N_4$ support in distilled water; b) preparing a catalyst precursor solution by adding the support solution with a ruthenium precursor and a palladium precursor so that the sum of weights of ruthenium and palladium as active components is 0.1 to 15 wt % based on the total weight of the catalyst including the support; and c) drying the catalyst precursor solution and then performing heat treatment in a hydrogen atmosphere.

In an embodiment, in step b), the weight ratio b/a of ruthenium b relative to palladium a may range from 0.25 to 10.

In an embodiment, in step c), the heat treatment in the hydrogen atmosphere may be performed at a temperature ranging from 250 to 500° C.

In addition, the present invention provides a selective hydrogenation method, comprising selectively hydrogenating a pyridine compound represented by Chemical Formula 2 in a mixture comprising a benzene compound represented by Chemical Formula 1 and the pyridine compound represented by Chemical Formula 2 using a Ru—Pd/g-$C_3N_4$ catalyst in which ruthenium and palladium as active components are loaded on a g-$C_3N_4$ support so that the sum of weights of the active components is 0.1 to 15 wt % based on the total weight of the catalyst including the support and the weight ratio b/a of ruthenium b relative to palladium a ranges from 0.25 to 10.

In an embodiment, the benzene compound may be at least one selected from among benzene, toluene, xylene, cyclohexyltoluene, diphenylmethane, benzyl alcohol, phenylethyl alcohol, methyl phenyl ether, and ethyl phenyl ether.

In an embodiment, the pyridine compound may be at least one selected from among pyridine, methylpyridine, ethylpyridine, cyclohexyl methylpyridine, benzylpyridine, pyridinemethanol, pyridylethanol, methoxypyridine, and ethoxypyridine.

In an embodiment, the amount of the Ru—Pd/g-$C_3N_4$ catalyst may be 0.5 to 10 wt % based on the total weight of reactants that are used, including the benzene compound and the pyridine compound.

In an embodiment, the selective hydrogenation may be performed at a temperature ranging from 20 to 200° C.

In an embodiment, the selective hydrogenation may be performed at a pressure ranging from 1 to 100 bar.

In addition, the present invention provides a selective hydrogenation method, comprising selectively hydrogenating a pyridine group in a compound represented by Chemical Formula 3 below using a Ru—Pd/g-$C_3N_4$ catalyst in which ruthenium and palladium as active components are loaded on a g-$C_3N_4$ support so that the sum of weights of the active components is 0.1 to 15 wt % based on the total weight of the catalyst including the support and the weight ratio b/a of ruthenium b relative to palladium a ranges from 0.25 to 10.

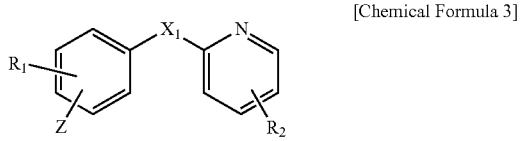
[Chemical Formula 3]

In Chemical Formula 3, Z represents hydrogen, a $C_1$-$C_6$ alkyl group, $C_1$-$C_6$ alkyl alcohol, $C_1$-$C_6$ alkylether or

(wherein Q is CH or N), $R_1$ represents hydrogen, a $C_1$-$C_6$ alkyl group, $C_1$-$C_6$ alkyl alcohol, $C_1$-$C_6$ alkylether or

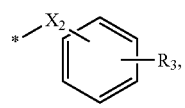

$R_2$ represents hydrogen, a $C_1$-$C_6$ alkyl group, $C_1$-$C_6$ alkyl alcohol or $C_1$-$C_6$ alkylether, $R_3$ represents hydrogen, a $C_1$-$C_6$ alkyl group, $C_1$-$C_6$ alkyl alcohol or $C_1$-$C_6$ alkylether, and $X_1$ or $X_2$ represents a single bond line, —$(CHR_4)_n$— (wherein n is an integer of 1 to 3, and $R_4$ is H, OH, or a $C_1$-$C_6$ alkyl group), —C(=$CH_2$)—, —C(O)—, or —N($R_5$)— (wherein $R_5$ is hydrogen or a $C_1$-$C_6$ alkyl group).

According to the present invention, in a hydrogenation reduction reaction of a compound using, as a hydrogenation catalyst, a composite comprising a g-$C_3N_4$ support and ruthenium and palladium serving as active metals, high reaction selectivity, in which a pyridine group can be more selectively hydrogenated upon the hydrogenation of a reaction system containing both a benzene group and a pyridine group, can result.

BRIEF DESCRIPTION OF DRAWING

FIG. 1 shows an electron microscopy image of a Ru—Pd/g-$C_3N_4$ catalyst according to the present invention.

DESCRIPTION OF SPECIFIC EMBODIMENTS

Unless defined otherwise, all technical and scientific terms used in this specification have the same meanings as would be generally understood by those skilled in the related art to which the present invention pertains. In general, the nomenclature used herein is well known and commonly used in the art.

In the specification, when any portion "includes" any component, this means that the portion does not exclude other components but may further include other components unless otherwise stated.

According to the present invention, a selective hydrogenation catalyst is configured such that active components, namely ruthenium and palladium, are loaded on a g-$C_3N_4$ support so that the sum of weights of the active components is 0.1 to 15 wt % based on the total weight of the catalyst including the support, and exhibits activity for the selective hydrogenation of a pyridine compound represented by Chemical Formula 2 below in a mixture comprising a benzene compound represented by Chemical Formula 1 below and the pyridine compound represented by Chemical Formula 2.

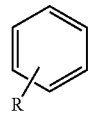
[Chemical Formula 1]

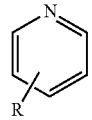
[Chemical Formula 2]

In Chemical Formulas 1 and 2, R is hydrogen, a $C_1$-$C_{13}$ alkyl or cycloalkyl group, a $C_7$-$C_{13}$ arylalkyl group, $C_1$-$C_{13}$ alkyl alcohol or $C_1$-$C_{13}$ alkylether.

The g-$C_3N_4$, which is an abbreviation of graphitic carbon nitride (graphite-phase carbon nitride), is a polymer material having a two-dimensional flat structure similar to graphene.

The sum of weights of ruthenium and palladium as the active components may fall in the range of 0.1 to 15 wt %, preferably 0.5 to wt %, and more preferably 2 to 8 wt % in terms of catalytic activity, based on the total weight of the catalyst including the support. If the amount of the active components is less than 0.1 wt %, active sites that show catalytic activity per unit area of the catalyst are not sufficiently exhibited. On the other hand, if the amount thereof exceeds 15 wt %, the extent of increase in the active sites due to the increase in the amount of the active components of the catalyst is insignificant, and thus an increase in the amount of loaded active components negates economic benefits.

In the active components, the weight ratio b/a of ruthenium b relative to palladium a falls in the range of 0.25 to 10, preferably 0.75 to 5, and more preferably 1 to 4, in order to maximize the selective hydrogenation activity.

If the weight ratio (b/a) of ruthenium relative to palladium is less than 0.25, the hydrogenation of the benzene group is still suppressed to induce selective hydrogenation of the pyridine group, but the absolute hydrogenation reduction rate of the pyridine group may decrease. Thus, the activity of the catalyst can also be reduced. On the other hand, if the weight ratio (b/a) exceeds 10, the hydrogenation rate of the benzene group may increase, and thus the Ru—Pd/g-$C_3N_4$ catalyst composite does not exhibit catalytic activity for selective hydrogenation of the pyridine group.

According to the present invention, a method of preparing the selective hydrogenation catalyst includes a) preparing a support solution by dispersing a g-$C_3N_4$ support in distilled water; b) preparing a catalyst precursor solution by adding the support solution with a ruthenium precursor and a palladium precursor so that the sum of weights of ruthenium and palladium as active components is 0.1 to 15 wt % based on the total weight of the catalyst including the support; and c) drying the catalyst precursor solution and then performing heat treatment in a hydrogen atmosphere.

In step b), the weight ratio b/a of ruthenium b relative to palladium a may range from 0.25 to 10.

The preparation of the g-$C_3N_4$ support may be performed through known methods, and is not particularly limited.

Specifically, the g-$C_3N_4$ support is dispersed in distilled water to give a support solution, after which the g-$C_3N_4$ support solution is added with a ruthenium precursor and a palladium precursor, thus preparing a catalyst precursor solution. Here, the addition temperature is not particularly limited, and may be room temperature. After the addition, the metal precursors and the g-$C_3N_4$ support may be stirred in order to realize uniform dispersion thereof.

In the active components, the kind of ruthenium precursor is not particularly limited, and is preferably selected from among ruthenium chloride, ruthenium acetylacetonate, ruthenium nitrosyl acetate, and ruthenium nitrosyl nitrate.

The kind of palladium precursor is not particularly limited, and is preferably palladium chloride or palladium nitrate, which is economical and has high loading efficiency.

Also, the aqueous solution in which the g-$C_3N_4$ support is dispersed and the palladium precursor and the ruthenium precursor are dissolved is dewatered to yield a g-$C_3N_4$ support loaded with the palladium precursor and the ruthenium precursor, and then dried. Here, the drying process may be performed through heating and/or under reduced pressure, and is preferably conducted using a vacuum drying device.

Thereafter, the dried catalyst composite is subjected to heat treatment in a hydrogen atmosphere. Heat treatment is conducted in order to control the extent of dispersion of active metals and the specific surface area thereof, remove impurities from the catalyst, and enhance bonding force of the active metals and the support, and the heat treatment is preferably performed at 250 to 500° C.

In the present invention, the heat treatment in a hydrogen atmosphere is preferably carried out in a hydrogen/argon or hydrogen/nitrogen atmosphere, and the proportion of hydrogen in the hydrogen/argon or hydrogen/nitrogen gas mixture is preferably 5 to 100%. Here, 100% hydrogen means that hydrogen is used alone.

Also, the present invention pertains to a selective hydrogenation method, including selectively hydrogenating a pyridine compound represented by Chemical Formula 2 in a mixture of a benzene compound represented by Chemical Formula 1 and the pyridine compound represented by Chemical Formula 2 using the Ru—Pd/g-$C_3N_4$ catalyst composite.

The hydrogenation rate of the pyridine group is preferably 75% or more, more preferably 80% or more, and most preferably 95% or more.

The benzene compound is preferably at least one selected from among benzene, toluene, xylene, cyclohexyltoluene, diphenylmethane, benzyl alcohol, phenylethyl alcohol, methyl phenyl ether, and ethyl phenyl ether, and the pyridine compound is preferably at least one selected from among pyridine, methylpyridine, ethylpyridine, cyclohexyl methylpyridine, benzylpyridine, pyridine methanol, pyridylethanol, methoxypyridine, and ethoxypyridine.

When the selective hydrogenation of the pyridine compound in the mixture comprising the benzene compound and the pyridine compound is carried out using the Ru—Pd/g-$C_3N_4$ catalyst composite, the pyridine group is more selectively hydrogenated than the benzene group.

The benzene compound has high solubility with respect to the pyridine compound, and is maintained in a liquid phase at the hydrogenation temperature depending on the type of benzene compound. In the hydrogenation of the pyridine compound, the benzene compound is suitable for use as a solvent for dissolving the pyridine compound. Furthermore, the benzene compound does not contain reactive sites having high reactivity and does not cause changes in functional groups or drastic changes in chemical properties upon hydrogenation, and thus constant reaction conditions may be provided during the reaction process.

In the selective hydrogenation method, the Ru—Pd/g-$C_3N_4$ catalyst is preferably used in an amount of 0.1 to 10 wt % based on the total weight of reactants that are used. If the amount of the Ru—Pd/g-$C_3N_4$ catalyst is less than 0.1 wt %, the activity of the catalyst is not sufficiently exhibited. On the other hand, if the amount of the Ru—Pd/g-$C_3N_4$ catalyst exceeds 10 wt %, economic benefits in terms of improving the activity of the catalyst, depending on the amount of catalyst, is ignored.

The selective hydrogenation is preferably carried out at a temperature ranging from 20 to 200° C. and a pressure ranging from 1 to 100 bar.

According to the present invention, the selective hydrogenation catalyst may also be used as a catalyst for selective hydrogenation in a molecule. An embodiment of the present invention pertains to a selective hydrogenation method, including selectively hydrogenating a pyridine group in a compound represented by Chemical Formula 3 below using the Ru—Pd/g-$C_3N_4$ catalyst.

[Chemical Formula 3]

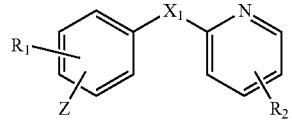

In Chemical Formula 3, Z represents hydrogen, a $C_1$-$C_6$ alkyl group, $C_1$-$C_6$ alkyl alcohol, $C_1$-$C_6$ alkylether or

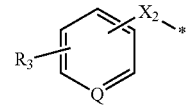

(wherein Q is CH or N), $R_1$ represents hydrogen, a $C_1$-$C_6$ alkyl group, $C_1$-$C_6$ alkyl alcohol, $C_1$-$C_6$ alkylether or

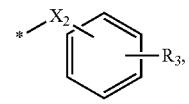

$R_2$ represents hydrogen, a $C_1$-$C_6$ alkyl group, $C_1$-$C_6$ alkyl alcohol or $C_1$-$C_6$ alkylether, $R_3$ represents hydrogen, a $C_1$-$C_6$ alkyl group, $C_1$-$C_6$ alkyl alcohol or $C_1$-$C_6$ alkylether, and $X_1$ or $X_2$ represents a single bond line, —$(CHR_4)_n$— (wherein n is an integer of 1 to 3, and $R_4$ is H, OH, or a $C_1$-$C_6$ alkyl group), —C(=$CH_2$)—, —C(O)—, or —N($R_5$)— (wherein $R_5$ is hydrogen or a $C_1$-$C_6$ alkyl group).

Upon the selective hydrogenation reaction using the Ru—Pd/g-$C_3N_4$ catalyst, the compound represented by Chemical Formula 3 is subjected to selective hydrogenation of a pyridine group therein, thus obtaining a compound represented by Chemical Formula 4 below.

[Chemical Formula 4]

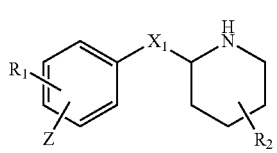

When the compound of Chemical Formula 3 in which Z is

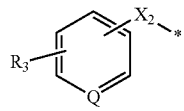

and Q is N is hydrogenated using the Ru—Pd/g-C₃N₄ catalyst, a compound represented by Chemical Formula 5 below may be obtained.

[Chemical Formula 5]

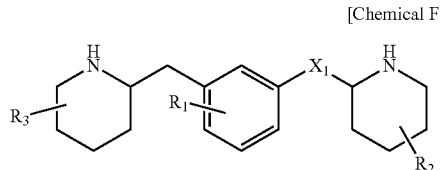

In the following description of preferred embodiments of the present invention, detailed descriptions of known functions and components incorporated herein will be omitted when the same may make the subject matter of the present invention unclear.

Furthermore, descriptions of embodiments and drawings of the present invention disclosed herein are only for the purpose of illustration of the preferred embodiments of the present invention, and are not intended to represent all of the technical ideas of the present invention, and thus a variety of equivalents and modifications able to substitute therefor may be provided at the point of time of filing of the present invention.

Hereinafter, a detailed description will be given of a Ru—Pd selective hydrogenation catalyst and a selective hydrogenation process using the same according to the present invention through the following examples and comparative examples, with reference to the appended drawing.

<Preparation Example> Preparation of Ru—Pd/g-C₃N₄ Catalyst

1) Preparation of g-C₃N₄ Support 6 g of melamine and 372 mg of 2,4,6-triaminopyrimidine were mixed with 250 mL of ethanol and stirred at 100° C. for 16 hr. After stirring, vacuum drying was performed. 6 g of the dried carbon nitride precursor powder was mixed with 6.78 g of lithium chloride and 8.22 g of potassium chloride, followed by a condensation reaction using a tubular burning machine. Here, nitrogen gas was allowed to flow at a flow rate of 500 cc/min, and the temperature was elevated to 550° C. at a rate of 12° C./min and was maintained at 550° C. for 4 hr. The obtained brown powder was repetitively filtered with water at 90° C., thus removing both lithium chloride and potassium chloride. Thereby, g-C₃N₄ was yielded as the support.

2) Preparation of 2.5 wt % Ru-2.5 wt % Pd/g-C₃N₄

1 g of g-C₃N₄ was dispersed in 10 mL of distilled water. 69.7 mg of ruthenium chloride, corresponding to 2.5 wt %, and 68 mg of palladium nitrate, corresponding to 2.5 wt %, were dissolved in 2 mL of distilled water. Thereafter, the g-C₃N₄-dispersed solution was added with the metal precursor solution and stirred at room temperature for 30 min. Thereafter, vacuum drying was performed, followed by heat treatment in a hydrogen atmosphere using a tubular burning machine. Here, a 5 mol % hydrogen/argon gas was allowed to flow at a flow rate of 350 cc/min, and the temperature was elevated to 350° C. at a rate of 5° C./min and was then maintained at 350° C. for 3 hr. FIG. 1 shows a transmission electron microscopy image of the 2.5 wt % Ru-2.5 wt % Pd/g-C₃N₄ thus synthesized.

3) Preparation of 2.5 wt % Ru-2.5 wt % Pd/Al₂O₃

1 g of alumina was dispersed in 10 mL of distilled water. 69.7 mg of ruthenium chloride, corresponding to 2.5 wt %, and 68 mg of palladium nitrate, corresponding to 2.5 wt %, were dissolved in 2 mL of distilled water. Thereafter, the alumina-dispersed solution was added with the metal precursor solution and stirred at room temperature for 30 min. Thereafter, vacuum drying was performed, followed by heat treatment in a hydrogen atmosphere using a tubular burning machine. Here, a 5 mol % hydrogen/argon gas was allowed to flow at a flow rate of 350 cc/min, and the temperature was elevated to 350° C. at a rate of 5° C./min and was then maintained at 350° C. for 3 hr.

4) Preparation of 2.5 wt % Ru-2.5 wt % Pd/C 1 g of activated carbon was dispersed in 10 mL of distilled water. 69.7 mg of ruthenium chloride, corresponding to 2.5 wt %, and 68 mg of palladium nitrate, corresponding to 2.5 wt %, were dissolved in 2 mL of distilled water. Thereafter, the activated carbon-dispersed solution was added with the metal precursor solution and stirred at room temperature for 30 min. Thereafter, vacuum drying was performed, followed by heat treatment in a hydrogen atmosphere using a tubular burning machine. Here, a 5 mol % hydrogen/argon gas was allowed to flow at a flow rate of 350 cc/min, and the temperature was elevated to 350° C. at a rate of 5° C./min and was then maintained at 350° C. for 3 hr.

<Examples 1 to 3 and Comparative Examples 1 to 4> Selective Pyridine Reduction Depending on the Type of Catalyst Selective pyridine reduction was conducted after adding 81.9 mmol pyridine, 81.9 mmol benzene, and a metal-loaded catalyst into a high-pressure reactor, without additional additives. As such, the amount of the metal-loaded catalyst was set such that the total mol of the metals in the catalyst was 0.4 mol % based on the total mol of benzene and pyridine.

The temperature was elevated to 150° C. for 45 min at a hydrogen pressure of 10 bar. After 45 min, the hydrogen pressure was increased to 40 bar and the reaction was carried out for 2 hr.

Table 1 below shows the results of measurement of hydrogenation conversion depending on the type of catalyst used for selective pyridine hydrogenation.

TABLE 1

| | | conversion (%) | |
|---|---|---|---|
| | Catalyst composition | Pyridine | Benzene |
| Example 1 | 4 wt % Ru - 1 wt % Pd/g-C₃N₄ | >99 | 5.4 |
| Example 2 | 2.5 wt % Ru - 2.5 wt % Pd/g-C₃N₄ | 98.8 | 2.4 |

TABLE 1-continued

| Catalyst composition | | conversion (%) | |
|---|---|---|---|
| | | Pyridine | Benzene |
| Example 3 | 1 wt % Ru - 4 wt % Pd/g-C$_3$N$_4$ | 75.7 | 2.0 |
| Comparative Example 1 | 5 wt % Ru/g-C$_3$N$_4$ | 97.5 | 95.1 |
| Comparative Example 2 | 5 wt % Pd/g-C$_3$N$_4$ | 49.3 | 4.9 |
| Comparative Example 3 | 2.5 wt % Ru - 2.5 wt % Pd/Al$_2$O$_3$ | 85.6 | 33.7 |
| Comparative Example 4 | 2.5 wt % Ru - 2.5 wt % Pd/C | >99 | 54.2 |

As is apparent from Table 1, when comparing the results of hydrogenation conversion of Examples 1 to 3 with those of Comparative Examples 1 to 4, the selective hydrogenation rate of pyridine was increased under the condition that both Ru and Pd were loaded on g-C$_3$N$_4$. The reactivity varied depending on the wt % of Ru—Pd. The total hydrogenation rate was increased with an increase in the amount of loaded ruthenium (Ru). The hydrogenation rates of pyridine and benzene were increased with an increase in the amount of loaded ruthenium, but the extent of increase thereof was W different, and thus the maximum selective hydrogenation rate of pyridine relative to benzene was present.

<Comparative Examples 5 to 8> Comparison with Commercially Available Catalyst Upon Selective Pyridine Hydrogenation Selective hydrogenation was carried out using a commercially available catalyst under the same reaction conditions as in Example 1.

Table 2 below shows the results of measurement of hydrogenation conversion depending on the type of catalyst used for selective pyridine hydrogenation.

TABLE 2

| Catalyst composition | | Conversion (%) | |
|---|---|---|---|
| | | Pyridine | Benzene |
| Example 1 | 2.5 wt % Ru - 2.5 wt % Pd/g-C$_3$N$_4$ | 98.8 | 2.4 |
| Comparative Example 5 | 5 wt % Ru/Al$_2$O$_3$ | >99 | 46.1 |
| Comparative Example 6 | 5 wt % Pd/Al$_2$O$_3$ | 0 | 0 |
| Comparative Example 7 | 5 wt % Ru/C | >99 | 57.4 |
| Comparative Example 8 | 5 wt % Pd/C | 45.2 | 1 |

As is apparent from Table 2, the commercially available ruthenium (Ru) catalyst considerably facilitated the hydrogenation of benzene, thus significantly deteriorating the selective hydrogenation effect of the pyridine group compared to the present invention. Also, the palladium (Pd) catalyst was varied in reactivity depending on the type of support. The alumina support did not catalyze the hydrogenation, and the carbon support was allowed to selectively hydrogenate only pyridine, but exhibited low conversion.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A selective hydrogenation method, comprising selectively hydrogenating a pyridine compound of Chemical Formula 2 below in a mixture of a benzene compound represented by Chemical Formula 1 below and the pyridine compound represented by Chemical Formula 2 using a Ru—Pd/g-C$_3$N$_4$ catalyst in which ruthenium and palladium as active components are loaded on a g-C$_3$N$_4$ support so that a sum of weights of the active components is 0.1 to 15 wt % based on a total weight of the catalyst including the support and a weight ratio (b/a) of the ruthenium (b) relative to the palladium (a) ranges from 0.25 to 10:

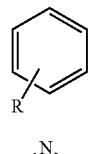

[Chemical Formula 1]

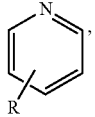

[Chemical Formula 2]

wherein, in Chemical Formulas 1 and 2, R is hydrogen, a C$_1$-C$_{13}$ alkyl or cycloalkyl group, a C$_7$-C$_{13}$ arylalkyl group, C$_1$-C$_{13}$ alkyl alcohol, or C$_1$-C$_{13}$ alkylether.

2. The selective hydrogenation method of claim 1, wherein a mass of the Ru—Pd/g-C$_3$N$_4$ catalyst is 0.5 to 10 wt % based on a total weight of reactants that are used.

3. The selective hydrogenation method of claim 1, performed at a temperature ranging from 20 to 200° C.

4. The selective hydrogenation method of claim 1, performed at a pressure ranging from 1 to 100 bar.

5. A selective hydrogenation method, comprising selectively hydrogenating a pyridine group in a compound represented by Chemical Formula 3 below using a Ru—Pd/g-C$_3$N$_4$ catalyst in which ruthenium and palladium as active components are loaded on a g-C$_3$N$_4$ support so that a sum of weights of the active components is 0.1 to 15 wt % based on a total weight of the catalyst including the support and a weight ratio (b/a) of the ruthenium (b) relative to the palladium (a) ranges from 0.25 to 10:

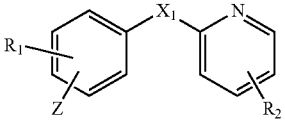

[Chemical Formula 3]

in Chemical Formula 3,

Z represents hydrogen; a C$_1$-C$_6$ alkyl group; C$_1$-C$_6$ alkyl alcohol; C$_1$-C$_6$ alkylether; or

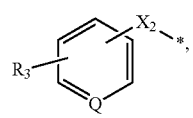

wherein Q is CH or N,

R$_1$ represents hydrogen, a C$_1$-C$_6$ alkyl group, C$_1$-C$_6$ alkyl alcohol, C$_1$-C$_6$ alkylether or

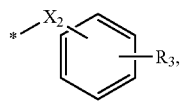

wherein * denotes a point of attachment to the Chemical Formula 3, $R_2$ represents hydrogen, a $C_1$-$C_6$ alkyl group, $C_1$-$C_6$ alkyl alcohol or $C_1$-$C_6$ alkylether, $R_3$ represents hydrogen, a $C_1$-$C_6$ alkyl group, $C_1$-$C_6$ alkyl alcohol or $C_1$-$C_6$ alkylether, and $X_1$ or $X_2$ represents a single bond line; —$(CHR_4)_n$—, wherein n is an integer of 1 to 3, and $R_4$ is H, OH, or a $C_1$-$C_6$ alkyl group, —C(=$CH_2$)—, —C(O)—; or —N($R_5$)—, wherein $R_5$ is hydrogen or a $C_1$-$C_6$ alkyl group.

6. A selective hydrogenation method, comprising selectively hydrogenating a pyridine compound in a mixture of a benzene compound and the pyridine compound using a Ru—Pd/g-$C_3N_4$ catalyst in which ruthenium and palladium as active components are loaded on a g-$C_3N_4$ support so that a sum of weights of the active components is 0.1 to 15 wt % based on a total weight of the catalyst including the support and a weight ratio (b/a) of the ruthenium (b) relative to the palladium (a) ranges from 0.25 to 10:

wherein the benzene compound is at least one selected from among benzene, toluene, xylene, cyclohexyltoluene, diphenylmethane, benzyl alcohol, phenylethyl alcohol, methyl phenyl ether, and ethyl phenyl ether, and the pyridine compound is at least one selected from among pyridine, methylpyridine, ethylpyridine, cyclohexyl methylpyridine, benzylpyridine, pyridinemethanol, pyridylethanol, methoxypyridine, and ethoxypyridine.

* * * * *